United States Patent
Wendt et al.

(10) Patent No.: US 10,765,657 B2
(45) Date of Patent: Sep. 8, 2020

(54) SELAMECTIN FOR TREATMENT OF SEA LICE INFESTATIONS

(71) Applicant: Zoetis Services LLC, Florham Park, NJ (US)

(72) Inventors: John Adam Wendt, Kalamazoo, MI (US); David Jose Asper, Kalamazoo, MI (US); Stacy Ross, Kalamazoo, MI (US)

(73) Assignee: Zoetis Services LLC, Parsippany, NJ (US)

( * ) Notice: Subject to any disclaimer, the term of this patent is extended or adjusted under 35 U.S.C. 154(b) by 155 days.

(21) Appl. No.: 14/367,977

(22) PCT Filed: Feb. 26, 2014

(86) PCT No.: PCT/US2014/018506
§ 371 (c)(1),
(2) Date: Jun. 23, 2014

(87) PCT Pub. No.: WO2014/134101
PCT Pub. Date: Sep. 4, 2014

(65) Prior Publication Data
US 2015/0366837 A1    Dec. 24, 2015

Related U.S. Application Data

(60) Provisional application No. 61/769,484, filed on Feb. 26, 2013.

(51) Int. Cl.
| | | |
|---|---|---|
| *A61K 31/00* | (2006.01) | |
| *A23K 20/00* | (2016.01) | |
| *A23K 50/00* | (2016.01) | |
| *A61K 47/00* | (2006.01) | |
| *A61K 31/352* | (2006.01) | |
| *A61K 45/06* | (2006.01) | |
| *A61K 31/7048* | (2006.01) | |
| *A23K 20/163* | (2016.01) | |
| *A23K 20/10* | (2016.01) | |
| *A23K 50/80* | (2016.01) | |
| *A23K 20/158* | (2016.01) | |
| *A23K 20/147* | (2016.01) | |
| *A61K 9/00* | (2006.01) | |
| *A61K 47/36* | (2006.01) | |
| *A61K 47/38* | (2006.01) | |
| *A61K 47/44* | (2017.01) | |

(52) U.S. Cl.
CPC ............ *A61K 31/352* (2013.01); *A23K 20/10* (2016.05); *A23K 20/147* (2016.05); *A23K 20/158* (2016.05); *A23K 20/163* (2016.05); *A23K 50/80* (2016.05); *A61K 9/0019* (2013.01); *A61K 31/7048* (2013.01); *A61K 45/06* (2013.01); *A61K 47/36* (2013.01); *A61K 47/38* (2013.01); *A61K 47/44* (2013.01); *Y02A 40/818* (2018.01)

(58) Field of Classification Search
None
See application file for complete search history.

(56) References Cited

U.S. PATENT DOCUMENTS

| | | |
|---|---|---|
| 5,981,500 A | 11/1999 | Bishop et al. |
| 6,486,128 B1 * | 11/2002 | Huq ..................... A01N 43/90 514/30 |
| 6,538,031 B1 | 3/2003 | Schmid |
| 6,797,701 B2 | 9/2004 | Lukas et al. |
| 8,128,943 B2 | 3/2012 | Bouvier et al. |
| 2012/0035122 A1 | 2/2012 | Vaillancourt et al. |

FOREIGN PATENT DOCUMENTS

| | | |
|---|---|---|
| EP | 0 379 341 | 7/1990 |
| WO | 92/08352 | 5/1992 |
| WO | 94/15944 | 7/1994 |
| WO | 2009/053466 | 4/2009 |

OTHER PUBLICATIONS

Fisher et al., Intern. J. Appl. Res. Vet. Med., 2007, vol. 5, No. 3, pp. 87-96.*
PCT International Search Report, PCT/US2014/018506, dated Apr. 23, 2014 (4 pages).

* cited by examiner

*Primary Examiner* — Sikarl A Witherspoon
(74) *Attorney, Agent, or Firm* — Paul M. Misiak

(57) ABSTRACT

The invention describes a method for treating a parasitic infection or infestation, particularly sea lice, in a fish by administering an effective amount of selamectin.

5 Claims, No Drawings

SELAMECTIN FOR TREATMENT OF SEA LICE INFESTATIONS

FIELD OF THE INVENTION

This invention describes compositions and methods of using selamectin for treatment against sea lice infestations in fish.

BACKGROUND

Sea lice are parasitic crustaceans/copepods within the order Siphonostomatoida, family Caligidae that feed on the mucus, epidermal tissue, and blood of host marine fish. Johnson et al, *Parasitol Res* (2002) 88: 789-796. Sea lice are prevalent parasites, particularly on salmonids, and, when present in high numbers, can cause serious disease and ultimately host death. In fish farms, where highly concentrated fish populations are present, sea lice can have a devastating effect on the stock.

In 2006, total salmonid marine production was 1.7 million tons, worth US $8.4 billion. See FAO Fisheries and Aquaculture Information and Statistics Service 2008, Aquaculture Production 1950-2006. Available data indicates sea lice cost from € 0.1 to € 0.2 $kg^{-1}$ of fish. Mark J Costello, The global economic cost of sea lice to the salmonid farming industry, *Journal of Fish Diseases*, v. 32(1), pgs 115-118 (2009). However, without treatment measures, sea lice would cost the industry at least four times more and probably increase to levels such as to cause significant direct and indirect mortality, to stock. Mustafa et al, *Canadian Veterinary Journal* 42, 54-56 (2001). Existing regional estimates for the cost of sea lice ranged from 4% of production value for Atlantic Canada to 7-10% in Scotland. Rae et al, *Pest Management Science* 58, 515-520 (2002)). Notably, Costello et al., supra, indicates a cost of 6% of the value of fish production for the countries affected by sea lice.

To date, available treatment regimens against sea lice infestations have been very limited, i.e., SLICE® (macrocyclic lactone—emamectin benzoate; U.S. Pat. No. 6,486,128 B1), being the only significant oral commercial treatment available. Additional ectoparasiticidal compounds have been explored, such as those described in U.S. Pat. No. 8,128,943 B2 and U.S. Pat. No. 6,538,031 B1, but no successful treatment agents based on these disclosures have emerged. Additionally, studies have been conducted on vaccine compositions targeting antigens present in sea lice, but no products using the vaccine approach have emerged either.

Accordingly, SLICE® has been widely used and as a result, significant resistance amongst sea lice populations has arisen, thought to be associated with its macrocyclic lactone structure, which occurs in other parasitic disease states targeted by macrocyclic lactones.

Accordingly, a need exists for a novel agent capable of treating sea lice infestations in fish, particularly in farmed fish populations, that is safe and selective against the target parasite and is capable of treating sea lice populations showing emamectin resistance.

Selamectin is a macrocyclic lactone used as a topical parasiticide and antihelminthic for dogs and cats. The antiparasitic activity of selamectin, a compound belonging to the class of avermectins, was disclosed in International Patent Application WO1994/15944 (Example 5) and is currently marketed as a topical pour-on for companion animal (dogs and cats) use under the trade name, Revolution®.

Like selamectin, emamectin also is an avermectin derivative and a macrocyclic lactone. Thus, one would expect sea lice resistance observed for emamectin to co-exist with selamectin. The invention surprisingly demonstrated that selamectin overcomes many of the disadvantages and resistance mechanisms associated with emamectin/SLICE®, in part due to its potency.

SUMMARY

The invention describes compositions comprising selamectin for treating a parasitic infestation in a fish; particularly, ectoparasites. More particularly, the parasite is sea lice. Thus, according to the invention, there is provided a method of treating or preventing a sea lice infestation in a fish, comprising administering to the fish or directly to the sea lice, selamectin, and veterinarily acceptable salts thereof.

In another aspect of the invention, selamectin is capable of treating emamectin resistant sea lice. In yet another aspect of the invention, selamectin is capable of treating both naïve sea lice and emamectin resistant sea lice.

In yet another aspect of the invention, the parasitic infestation is an ectoparasite infestation. More particular still, the ectoparasite is a copepod; specifically the copepod is sea lice. In another aspect of the invention, the sea lice is *Lepeophtheirus* or *Caligus* species, specifically *Lepeophtheirus salmonis*, *Caligus celmensi*, *Caligus curtus*, *Caligus dussumieri*, *Caligus elongates*, *Caligus longicaudatus*, *Caligus rogercresseyi* or *Caligus stromii*.

In yet another aspect of the invention, the fish is a farmed fish. In another aspect of the invention, the fish is selected from the group consisting of carp, tuna, tilapia, cod, halibut, trout, and salmon. More particularly, the fish is a marine fish. More particular still, the fish is a salmon.

In one aspect of the invention, the selamectin composition is a solid composition. In particular, selamectin is mixed with at least one veterinary acceptable solid carrier to prepare a concentrated mixture that can be subsequently diluted by adding a greater amount of a veterinary solid carrier to the mixture. Either solid selamectin composition can be admixed with fish feed.

In another aspect, the invention is directed to a solid composition comprising: about 50-95% corn starch, about 5-15% pre-gel corn starch, about 1-10% a disintegrant which prevents binding, particularly microcrystalline cellulose, and about 0.1-5% selamectin. In yet another aspect, the composition comprises about 70-90% corn starch, about 8-12% pre-gel corn starch, about 3-7% a disintegrant which prevents binding, particularly microcrystalline cellulose, and about 0.1-3% selamectin. In yet another aspect, the composition comprises about 85% corn starch, about 10% pre-gel corn starch, about 5% microcrystalline cellulose, and about 0.2-1% selamectin, and more particularly, about 0.3-0.5%. Similarly, these solid corn starch compositions can be admixed with fish feed to attain a therapeutically effective amount of selamectin. The solid selamectin compositions can further comprise an antioxidant.

In another aspect of the invention, the solid composition, particularly, the corn starch composition can be admixed with a fish feed composition and an oil, solvent, or mixture thereof, to facilitate selamectin composition adherence to the feed composition prior to dosing.

In another aspect of the invention, the selamectin composition is a liquid composition. In particular, the liquid composition comprises selamectin and at least one of an oil, solvent, or mixture thereof.

In another aspect, the invention is directed to a liquid composition comprising an oil, selamectin, and optionally, at least one antioxidant. In yet another aspect, the oil is selected from at least one of a vegetable oil, fish oil, or other oil. In one aspect of the invention, the oil is a Miglyol and the antioxidant is butylated hydroxyanisole (BHA) and/or butylated hydroxytoluent (BHT). In yet another aspect of the invention, the miglyol is Miglyol 812. The liquid selamectin compositions can be admixed with fish feed to attain a therapeutically effective amount of selamectin.

In another aspect, the invention is directed to a liquid composition, for example, Revolution®. Revolution® comprises about 60 mg/mL and 120 mg/ML selamectin in at least one solvent. The composition further comprises at least one antioxidant. The Revolution® product cart be diluted with an oil, solvent, or mixture thereof, prior to admixture with fish feed to attain a therapeutically effective amount of selamectin.

A therapeutically effective oral dose ranges from about 0.5 to 700 µg/kg/day, more particularly 5 to 300 µg/kg/day, more particularly 20 to 200 µg/kg/day, and even more particularly 50-150 µg/kg/day, and even more particularly, 100 µg/kg/day. The duration of administration can be from a few hours or days up to two years.

In another aspect of the invention, the invention provides a liquid and solid composition comprising selamectin for admixture with fish feed for oral administration to fish. More particularly, the feed composition comprises at least one of fat, nutrients, carbohydrate, and protein. The feed composition is admixed with the solid selamectin composition or the liquid selamectin composition. In one aspect, the feed composition is a pellet. The liquid or solid selamectin composition is added to the pellet by admixture. The solid selamectin composition is admixed with the fish feed with an oil, solvent, or mixture thereof, to ensure that the selamectin composition adheres to the fish feed.

In yet another aspect of the invention, selamectin is administered to the fish by immersing (i.e., bath treatment) the fish in a solution comprising selamectin and water. A concentration range of selamectin from about 0.001 ppm to about 200 ppm, preferably about 1 ppm to about 200 ppm, more preferably about 10 ppm to about 150 ppm, and even more preferably from about 20 ppm to about 100 ppm, based on total bath volume is contemplated. The concentration of selamectin during application depends on the manner and duration of treatment and also on the age and condition of the fish being treated. A typical immersion time ranges from about 15 minutes to about 4 hours, in particular from about 30 minutes to about 1 hour. Selamectin can be dissolved or suspended in the surrounding water of the fish and sea lice. The bath can contain further common excipients known in the art for preparing aqueous solutions, for example, stabilizers, antifoaming agents, viscosity modifiers, binders, and tackifiers.

In yet another aspect of the invention, selamectin is injected into the fish. More particularly, selamectin is injected into the fish intraperitoneally (IP) or intramuscularly (IM).

In yet anther aspect of the invention, selamectin can be administered in combination with an additional active agent, for example, the organophosphates dichlorvos (Aquagard® Novartis) and Azamethiphos (Salmosan® Novartis), or hydrogen peroxide (Salartect® Brenntag, Paramove® Solvay-Interox), or the synthetic pyrethoids, cypermethrin (Excis® Vericore) and deltamethrin (Alphamax® Alpharma), benzoylureas of U.S. Pat. No. 6,538,031 B1, diphenyloxazoles of U.S. Pat. No. 8,128,943 B2, isoxazolines of US Patent Publication No. US2013/0065846 and Patent Publication Nos. WO2011/157733 and WO2013/119442 (particularly Compound A), and the spiroisoxazolines of U.S. Pat. No. 8,466,115 B2, an antigen, inactivated or killed virus or bacteria, adjuvant, and mixtures thereof. Co-administration can occur simultaneously, sequentially or separately.

In another aspect of the invention, selamectin is administered to a single fish. In another aspect of the invention, selamectin is administered to a plurality of fish.

In yet another aspect, the invention describes a kit comprising any one of the selamectin compositions and instructions for administration of the composition to fish.

In another aspect, the invention is directed to the use of selamectin in treating a sea lice infestation in fish.

In another aspect, the invention is directed to use of selamectin in the preparation of a medicament for treating sea lice infestation in fish.

Other objects, features and advantages of the invention will become apparent from the following detailed description. It should be understood, however, that the detailed description and the specific examples, while indicating specific aspects of the invention, are given by way of illustration only, since various changes and modifications within the spirit and scope of the invention will become apparent to those skilled in the art from this detailed description.

DETAILED DESCRIPTION

For purposes of the invention, as described and claimed herein, the following terms and phrases are defined as follows:

"Additional active agent(s)" as used herein, unless otherwise indicated, refers to other antiparasitic compounds or products, antigens, adjuvants, inactivated or killed viruses or bacteria, and the like, that provide a therapeutically effective amount of said agent(s) that are useful for the treatment of a parasitic infection in a fish, as described herein.

The term "resistance" particularly "emamactin resistance" refers to reduced potency of a compound as compared to naïve parasites, particularly sea lice.

"Fish" as used herein include food fish, breeding fish and aquarium, or pond fish of all ages occurring in freshwater, sea water (e.g., marine) and brackish water. The food fish and breeding fish include, for example, carp, eel, trout, whitefish, salmon, roach, rudd, chub, arctic charr, sturgeon, plaice, halibut, turbot, flounder, striped bass, yellowtail, grouper, cod, sole, carp, Japanese yellowtail (*Seriola quinqueradiata*), Japanese eel (*Anguilla japonica*), tuna, red sea bream (*Pagurus major*), sea bass (*Dicentrarchus labrax*), grey mullet (*Mugilus cephalus*), pompano, gilthread seabream (*Sparus auratus*), Tilapia spp., Cichlidae species such as plagioscion, channel catfish and "salmon". Within the scope of this invention will be understood as comprising all representatives of the family Salmonidae, especially of the subfamily salmonini and, preferably, the following species: *Salmo salar* (Atlantic salmon); *Salmo trutta* (brown or sea trout); *Oncorhynchus mykiss* (rainbow trout); and the Pacific salmon (*Oncorhynchus*): *O. gorbuscha; O. keta; O. nekra; O. kisutch, O. tshawytscha* and *O. mason*; also comprised are artificially propagated species such as *Salvelinus* species and *Salmo clarkia*.

In a preferred aspect of the invention, the fish are kept in sea water tanks, cages or nets. The cages and nets are moored in sea inlets such that a daily tidal flow of water passes through them in order to ensure a sufficient supply of oxygen and clean water. For tanks, there is a continual flow of sea water in and out of the tanks or at least scheduled flushing of fresh sea water to ensure sufficient water quality and oxygen to maintain fish health. In this artificial environment, the fish are fed and, if necessary, provided with medication until they mature sufficiently for marketing as edible fish or are selected for further breeding.

Extremely intensive cage stocking is maintained in these fish farms. In this pure monoculture, the exceedingly high fish densities coupled with the other stress factors cause the caged fish to become in general markedly more susceptible to disease, epidemics and parasites than their free-living co-species. In order to maintain healthy populations, the farmed fish are treated regularly with bactericides and/or antiparasitics, and are monitored.

"Sea lice" as used herein, unless otherwise indicated, refers to parasitic crustaceans (copepods) which feed through or upon the mucus and skin of its host, and are within the order Siphonostomatoida, family Caligidae. Two representatives of the class cause substantial losses in yield: *Lepeophtheirus* and *Caligus*. *Lepeophtheirus* has a brown, horseshoe-shaped carapace and *Caligus* is also brown, but smaller. Species within *Lepeophtheirus* include *Lepeophtheirus salmonis* and within *Caligus* include *Caligus celmensi, Caligus curtus, Caligus dussumieri, Caligus elongates, Caligus longicaudatus, Caligus rogercresseyi* and *Caligus stromii*. Sea lice also include the Copepodae [hoppers] of the genera *Ergasilus; Bromolochus; Chondracaushus; Elythrophora; Dichelestinum; Lamproglenz; Hatschekia; Legosphilus; Symphodus; Ceudrolasus; Pseudocycmus; Lemaea; Lemaeocera; Pennella; Achthares; Basanistes; Salmincola; Brachiella; Epibrachiella; Pseudotracheliastes*; and the familes: Ergasilidae; Bromolochidae; Chondracanthidae; Calijidae; Dichelestiidae; Philichthyidae; Pseudocycnidae; Lemaeidae; Lemaepotidae; Sphyriidae; and Cecropidae. Sea lice also includes substantially the free swimming larval stages of the respective adults.

These sea lice injure the fish by feeding on the scales, epithelium and the mucosa. When infestation is severe, these parasites also damage underlying dermis. If, moreover, infected salmon are kept in cooler waters, then they are normally no longer able to protect themselves from these pests. As a consequence, secondary infections and waterlogging will occur, even if the sea lice are removed. In extreme cases, severe wounding resulting from infestation by these parasites leads to further tissue damage caused by ultraviolet radiation or to the death of the fish from osmotic shock or the secondary infections.

"Therapeutically effective amount", as used herein, unless otherwise indicated, refers to an amount of selamectin that (i) treat the particular parasitic infection or infestation, (ii) attenuates, ameliorates, or eliminates one or more symptoms of the particular parasitic infection or infestation, or (iii) prevents or delays the onset of one or more symptoms of the particular parasitic infection or infestation described herein.

"Treatment", "treating", and the like, as used herein, unless otherwise indicated, refers to reversing, alleviating, preventing or inhibiting the parasitic infection, infestation, or condition. As used herein, these terms also encompass, depending on the condition of the fish, preventing the onset of a disorder or condition, or of symptoms associated with a disorder or condition, including reducing the severity of a disorder or condition or symptoms associated therewith prior to affliction with said infection or infestation. Thus, treatment can refer to administration of the compounds of the invention to a fish that is not at the time of administration afflicted with the infection or infestation. Treating also encompasses preventing the recurrence of an infection or infestation or of symptoms associated therewith as well as references to "control" (e.g., kill, repel, expel, incapacitate, deter, eliminate, alleviate, minimize, and eradicate).

Reference to treating a parasitic infestation "in" a fish is understood to constitute treatment of an external parasite, such as sea lice, which feeds "on" a fish and not necessarily exist inside the fish.

"Veterinary acceptable" as used herein, unless otherwise indicated, indicates that the substance or composition must be compatible chemically and/or toxicologically, with the other ingredients comprising a composition and/or the fish being treated therewith.

The compositions disclosed can be administered in a variety of ways. It should be noted that the composition can be administered alone or in combination with one or more veterinary acceptable carriers, stabilizers, preservatives, colorants, flavorants, and excipients.

Reference to "fish food", "fish feed", and "feed composition" indicates substances specially adapted for oral administration to fish. Particularly, a food substance comprising at least one of fats, nutrients, protein, vitamins, minerals, and carbohydrates in liquid, flake, granule, or pellet form, which is capable of adsorbing or being admixed with selamectin. Preferably, the fish food includes selamectin and at least one of corn starch, pregelatinized corn starch, protein, nutrients, vegetable oil and/or fish oil.

The compositions disclosed can be formulated with conventional carriers and excipients, which are selected in accord with ordinary practice. Aqueous formulations for injection are preferably prepared in sterile form, and when intended for injectable routes, generally are isotonic. Excipients include ascorbic acid and other antioxidants, chelating agents (e.g., EGTA and EDTA), carbohydrates (e.g., dextrin), hydroxyalkylcellulose, hydroxyalkylmethylcellulose, stearic acid, and the like. The pH of the formulations ranges from about 3 to about 11.

Examples of physiologically acceptable carriers for routes of administration other than oral administration include but are not limited to saline solutions (e.g., normal saline, Ringer's solution, PBS (phosphate-buffered saline); polysorbate 80; L-arginine; polyvinylpyrrolidone; α-D-glucopyranosyl; α-D-glucopyranoside (trehalose); and combinations, thereof. For example, trehalose can be present in the composition in an amount from about 2 to about 10% weight/volume of the composition. In another example, when trehalose and polysorbate 80 are both present in the composition, trehalose can be present in the amount of about 4 to about 6% wt./vol. and the polysorbate 80 can be present in the amount of about 0.001 to 0.01% (wt./vol.) and generally mixtures of various physiologically compatible salts including potassium and phosphate salts with or without sugar additives (e.g., glucose).

Suitable excipients for use in the immunogenic formulations are, for example, water, saline, dextrose, glycerol, and ethanol. Non-toxic auxiliary substances, such as wetting agents, buffers, stabilizers, or emulsifiers can also be added to the composition.

For each recipient, the total amount of the composition necessary for administration can be derived by routine practice of those skilled in the art. The exact amount of such compositions required may vary from fish to fish or stock to stock.

The formulations include those suitable for the foregoing administration routes. The formulations can conveniently be presented in unit dosage form and can be prepared by any of the methods well known in the art of veterinary science. In general, the formulations are prepared by uniformly and intimately bringing into association the active ingredient, selamectin, with liquid carriers (i.e., oils, solvents, or mixtures thereof) or finely divided solid carriers, or both, and then, if necessary, shaping the final feed product.

The oil phase of the emulsions of this invention can be constituted from known ingredients in a known manner. While the phase can comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier, which acts as a stabilizer. It is also preferred to include both an oil and a fat.

Veterinary carriers are materials useful for the purpose of administering the composition and can be solid, liquid or gaseous materials, which are otherwise inert or acceptable in the veterinary art and are compatible with the selamectin. These veterinary compositions can be administered orally, parenterally, or by any other desired route.

As indicated above, the present disclosure provides compositions and methods that employ selamectin for oral administration. In certain aspects of the present disclosure, the compound is used in the form of a powder, though other formulations may be appropriate. The oral feed compositions and formulations which follow are all contemplated in the fish food of the invention.

Exemplary oral non-toxic inert suitable excipients include, for example, fillers and extenders, binders, humectants, solution retarders, absorption accelerators, wetting agents, adsorbents or lubricants, which may have a solid, semisolid or liquid consistency. Such excipients are known to those of skill in the art.

Selamectin is added to the fish feed by customary methods, by simply mixing as a pure substance, such as a powder, or in a liquid, or in a formulated form mixed with edible, nontoxic excipients (i.e., oil, solvent, mixtures thereof, and solid carriers) in the form of a premix. Thus, selamectin may be formulated together with other minerals, salts, elements, vitamins, proteins, fats, colorants and/or flavorings to attain a final medicated fish feed.

It will be understood that the amount of the compound that is administered to a fish to achieve the desired effect can be substantially varied because of the favorable non-toxic properties of selamectin. In one aspect, selamectin is administered orally at about 0.5 to 700 µg/kg/day, more particularly 5 to 300 µg/kg/day, more particularly 20 to 200 µg/kg/day (i.e. µg compound per kg fish body weight per day). A dose of about 50 to about 150 µg/kg/day and about 100 µg/kg/day is also contemplated. The duration of administration can be from a few hours or days up to two years. In one aspect, selamectin is administered orally for a duration of 7-days. Selamectin can also be administered for a shorter (1, 2, 3, 4, 5, or 6 days) or longer (8, 9, 10, or more days) duration, and potentially, up to 2-years.

All conventional or special feed compositions can be used, and these preferably contain the customary balance of nutrients for a balanced diet. For example, the feed can be composed of vegetable matter, for example, hay, roots, cereals, cereal by-products, kelp, lettuce, and the like; animal matter, for example, meat, fats, bone meal, fish products, and the like; vitamins, for example vitamin A, D complex and B complex; protein; amino acids; inorganic substances, for example, lime and sodium chloride; and the like.

Feed concentrates contain the active compound in addition to edible substances, for example rye meal, corn meal, corn starch, soy bean meal or lime, where appropriate with other nutrients and builders, and proteins, mineral salts and vitamins. They can be produced by the customary mixing methods and subsequently diluted to achieve a therapeutically effective amount of selamectin.

When formulated as a feed, selamectin may be admixed with one or more fish-appropriate feedstuff. Alternatively or additionally, the premix may comprise other nontoxic material(s), which are typically though not exclusively carbohydrate-based, and are of sufficient granularity to facilitate thorough mixing when added to larger quantities of feedstuff. Other nutrients, proteins, mineral salts, and vitamins may be included in a selamectin premix.

The feed mixtures indicated are adjusted to be appropriate preferably for the rearing, fattening and harvesting of fish. When using a pre-mix of concentrated compound, it is generally then added to additional stores of untreated food. The optimum final concentration of selamectin will depend upon the amount of food to be consumed by the fish and can be readily determined by those of skill in the art. The type of food and its composition will be determined by the skilled artisan based upon the particular requirements of the species of fish and location or size.

In a preferred aspect of the invention, fish food can be combined with selamectin to form a pellet, for example, co-extrusion. The pellet may include ingredients such as corn starch, oil, such as herring oil or vegetable oil, and selamectin. Selamectin can be added to fish feed pellets by surface coating the pellets. In surface coating, a premix is typically suspended in fish oil and the suspension is poured onto the feed under mixing in a suitable mixer (ribbon or, cement-type mixer). A premix comprising selamectin can also be dusted onto feed pellets followed by the oil coat, which is referred to as the double-coating procedure. In a co-extrusion method, a premix of selamectin is blended with feed ingredients in a mixer. The blend is then conditioned and passed through an extruder under high heat and humidity conditions. The extruded pellets are then dried and coated with oil, if desired.

Additional aquaculture formulation techniques and compositions are described in Z. J. Shao, *Advanced Drug Delivery Reviews*, 50 (2001) 229-243, the contents of which is hereby incorporated by reference as if set forth fully herein.

Selamectin composition(s) can be prepared according to the following non-exclusive processes. As a liquid dosage form, selamectin can be dissolved in a solvent, oil, or mixture thereof, and can be further diluted with an oil, solvent, and mixture thereof. The term solvent encompasses both polar and non-polar solvents. Non-exclusive examples of a solvent include: SD alcohol 3A (denatured), methanol, ethanol, benzyl alcohol, isopropanol, acetone, methylene chloride, butyl diglycol, dimethylacetamide, dimethylformamide, polyoxyethylated ethers (for example, ethylene glycol monomethyl ether, diethylene glycol monomethyl ether, diethylene glycol monoethyl ether, dipropylene glycol monomethyl ether, dipropylene glycol monoethyl ether, and the like), propylene glycol, ethylene glycol, and the like, and mixtures thereof. The term oil, as defined herein, encompasses naturally derived and semisynthetic/synthetic monoglycerides, diglycerides, and triglycerides. Non exclusive examples of oils include vegetable oil (e.g., corn, coconut, cottonseed, olive, palm, peanut, sesame, soybean, safflower, sunflower, castor, almond, and the like), fish oil (e.g., herring, mackerel, anchovie, sardine, and the like), or other oil (e.g., mineral, polyethylene glycol, propylene glycol, propylene carbonate, glycerin, glycerol, triacetin, triethyl citrate, glyceryl stearates, glyceryl hexanoates, caprylic/capric glycerides (e.g., Miglyols (e.g., 810, 812, 818, 829, 840, and the like; Captex (e.g., 200, 300, 355, 500, 800, and the like), glyceryl cocoate, caprylic glycerides, glyceryl monooleate, glyceryl ricinoleate, capric glycerides, and the like. Further, the selamectin composition can be prepared by dissolving the selamectin in a mixture of at least one oil and at least one solvent. These selamectin compositions (i.e., premix and diluted compositions) can be applied directly to fish feed. For the solid compositions, an oil is generally added to the mixture to ensure the medicated composition adheres to the fish feed.

As a solid dosage form, selamectin can be mixed with a veterinary acceptable carrier (e.g., corn starch, pregelatinized corn starch, microcrystalline cellulose, carboxymethyl cellulose, mannitol, sugar (e.g., lactose, glucose, dextrose, sucrose, maltodextrin, and the like), kaolin, and the like, or mixture thereof) to prepare a concentrated solid. The concentrated solid can be mixed directly with fish feed or the concentrate can be subsequently mixed with an additional amount of at least one veterinary acceptable carrier to prepare a less concentrated solid admixture that can be directly mixed with fish feed. The fish feed and solid selamectin mixture can also be prepared by admixing with an oil or solvent, or mixture thereof, to enhance selamectin adherence to the feed. Fish feed comprises all available sources of fish food, including powders, granules, pellets, and the like. Fish feed further comprises food additives, e.g., fillers, vitamins, minerals, and other nutritional components.

In addition to the excipients (i.e., veterinary acceptable carriers, oils, solvents, and mixtures thereof), the liquid compositions can further comprise a surfactant. Surfactants are generally well known in the art. Non-exclusive examples of surfactants include, polysorbates, Tweens, poloxamers, sodium lauryl sulfate, sodium dodecylsulfate, and the like, and mixtures thereof. While concentrated compositions are sometimes preferred as commercial goods, the end user, e.g., for bath application or dietary admixture, normally uses compositions that are diluted with water, oil, solvent, or solid carrier (e.g., corn starch) which will have a substantially lower amount of selamectin.

Non-exclusive examples of various mixtures, admixtures, formulations, and compositions available for use include:

A. Pre-mix formulation: about 85% corn starch, about 10% pregelatinized corn starch, about 5% microcrystalline cellulose (MCC-PH105), and about 0.4% selamectin. An oil can be used to adhere the selamectin to the mixture, typically about 0.1% to about 2% oil can be used.

B. Liquid Concentrates: selamectin about 0.1-25%, preferably about 1-15%, more preferably about 2-12%, more preferably about 3-6%; the remaining volume can be adjusted with a solvent or an oil, and mixtures thereof, to 100%. The concentrate can further comprise a surfactant and/or at least one antioxidant.

C. Suspension Concentrates: selamectin about 0.5-75%, preferably about 10-50%; water about 24-94%, preferably about 30-88%; surfactant about 1-40%, preferably about 2-30%.

D. Wettable Powders: selamectin about 0.5-50%, preferably about 1-40%; surfactant about 0.5-20%, preferably about 1-15%; solid carrier about 5-99%, preferably about 15-98%.

E. Granulates: selamectin about 0.5-30%, preferably about 3-15%; solid carrier about 70-99.5%, preferably about 85-97%.

F. Emulsifiable Concentrates: selamectin about 25-50%; calcium dodecylbenzene sulfonate about 5-8%; castor oil polyethylene glycol ether about 5%; tributylphenol polyethylene glycol about 4-12%; ether cyclohexanone about 15-20%; and xylenes about 20-65%.

G. Extruder Granulate: selamectin about 0.5-10%; sodium ligninsulfonate about 2%; carboxymethyl cellulose about 1%; kaolin about 87%. Selamectin is mixed with the excipients and the mixture is ground and moistened with water. This mixture is extruded, granulated and then dried in a stream of air.

H. Coated Granulates: selamectin about 0.1-3%; polyethylene glycol about 3%; kaolin about 94%. The finely ground selamectin is uniformly applied, in a mixer, to the kaolin moistened with polyethylene glycol. Non-dusty coated granulates are obtained in this manner.

I. Suspension Concentrate: selamectin about 0.5-40%; ethylene glycol about 10%; nonylphenol polyethylene glycol ether about 6%; sodium ligninsulfonate about 10%; carboxymethyl cellulose about 1%; about 37% aqueous formaldehyde solution (0.2%); silicone oil in the form of a 75% aqueous emulsion (0.8%); and about 32% water. The finely ground selamectin is homogeneously mixed with the excipients, giving a suspension concentrate from which suspensions of any desired concentration can be obtained by dilution with water.

J. Injection Formulations: Ampoule containing selamectin, disodium pamidronat pentahydrate and water. After dissolution (3 mg/mL selamectin), the solution can be used for injection. Selamectin 15.0 mg, mannitol 250 mg, and water for injection 5 mL.

K. Pellet Formulation: Selamectin about 0.1-20%, fish or vegetable oil about 1-5%; corn starch about 75-98%. Ingredients are mixed into a pellet formulation with the oil acting as an adherent and flavorant.

Selamectin containing compositions can also be used in combination with additional active agents. Such combinations are selected based on the condition to be treated, cross-reactivities of ingredients, and pharmacological properties of the combination. For instance, multifunctional agents, such as polyvalent vaccines are preferable in fish treatment, thus the composition may be administered with antigens targeting other diseases. These compounds and compositions can be administered together with, or in the same course of, therapy with the compounds and compositions described herein. The individual components of the combination can be administered either sequentially or simultaneously in separate or combined veterinary formulations.

Compounds for use in the compositions and methods of the invention may be synthesized by synthetic routes that include processes analogous to those well known in the chemical arts (e.g. Patent Application publication WO1994/15944), particularly in light of the description contained herein or may be purchased from commercially available sources. A skilled artisan will appreciate that other suitable starting materials, reagents, and synthetic routes may be used to synthesize selamectin. Alternatively, selamectin can be purchased commercially in pure form, or in a liquid spot-on formulation (i.e., Revolution®) and diluted for use in new lower concentration premix compositions for admixture with fish feed for oral administration or diluted in a solvent for immersion treatment.

Some aspects of the invention are illustrated by the following Examples. It is to be understood, however, that the aspects of the invention are not limited to the specific details of these Examples, as other variations thereof will be known, or apparent in light of the instant disclosure, to one of ordinary skill in the art.

EXAMPLES

Example 1

Experimental diets containing selamectin were administered to 15×2 m diameter tanks of 75 fish by voluntary feeding from Day 0 to Day 6. The compound was used at three doses equivalent to 1×, 4× and 8× the standard molar dose of emamectin benzoate (the active in SLICE®) used for a positive control group. The study evaluated the three concentrations of test material in comparison to a negative control (placebo) and a positive control. Each group was run as triplicate tanks. In each group, sea lice were evaluated using a representative sample of 5 fish per tank on Day −1 (pre-treatment) and 10 fish per tank on days 10 and 30 (4 and 24 days post-treatment).

The prophylactic effect of treatment was determined by removing lice and using further sea lice challenges at intervals. All adult lice were removed from remaining fish following Day 30 and a further sea lice challenge took place on Day 37 (31 days post treatment) and lice counts and tissue samples taken from 10 fish per tank on Day 60 (53 days post treatment).

All adult lice were removed from remaining fish following Day 64 and 12 fish per tank were moved to 15×1 m diameter tanks. On Day 67 (61 days post-treatment) the fish in these 1 m tanks received a further sea lice challenge and on Day 90 (84 days post-treatment) lice counts and tissue samples were taken from 10 fish per tank.

On Day 76 (70 days post-treatment) the fish remaining in 2 m tanks received a further naïve sea lice challenge and on Day 99 (93 days post-treatment) lice counts and tissue samples were taken from 10 fish per tank.

Results: In naïve sea lice which have never come in contact with an avermectin deravitive, selamectin at 40 µg/kg/day demonstrated 99.6% prophylactic efficacy at 4.4 weeks and 68.4% prophylactic efficacy at 10 weeks. A 160 µg/kg/day dose of selamectin reached 100% prophylactic efficacy at 4.4 weeks and 98.5% prophylactic efficacy out to 10 weeks. Thus, at 160 µg/kg/day selamectin was very efficacious. Emamectin at the commercially licensed value of 50 µg/kg/day showed 100% prophylactic efficacy at 4.4 weeks and 72.9% out to 10 weeks. Thus, in naïve sea lice, both emamectin and selamectin were efficacious, although only selamectin at 160 µg/kg/day demonstrated commercially viable protection out to 10 weeks.

Example 2

Tests were conducted using either naïve or emamectin benzoate resistant sea lice produced from laboratory-maintained cultures. Each bioassay was performed using similar numbers of male and female pre-adult and adult sea lice, *Lepeophtheirus salmonis*.

Groups of 10 sea lice in three replicates per concentration were exposed to each test material at five concentrations plus negative control. All groups were exposed to solvent at the same concentration. Exposures were in petri dishes at constant temperature (approximately 12° C.) for 24 hours. At the end of the exposure period sea lice mortality and morbidity was assessed. Lice exposed to the lowest treatment dose of each compound were examined first, thereafter subsequent doses in increasing order.

Lice were scored as dead, moribund or apparently healthy according to predetermined criteria. Percent efficacy was calculated for each compound at each dose. The data was also used to establish survival curves and establish $LC_{50}$ and $EC_{50}$ values as depicted in Table 1.

Concentration values are in parts per billion (ppb). Static bioassays were conducted over 24 hours using 0.2% DMSO in fresh seawater filtered through a nylon mesh screen with nominal mesh size of 100×100 µm, circa. The temperature was maintained at about 10-12° C. The sea lice (*L.salmonis*) strains used were maintained at Marine Environmental Research Laboratory, University of Stirling, Machrihanish, Argyll, PA28 6PZ, United Kingdom.

TABLE 1

Sea Lice Efficacy

| Compound | Lice Strain | Adult males $EC_{50}$ | Adult females $EC_{50}$ | Viable Control Lice (%) |
| --- | --- | --- | --- | --- |
| Selamectin | Naïve | 3.21 | 10.68 | 100 |
| Emamectin benzoate | Naïve | 112 | 29 | 100 |
| Selamectin | Resistant | 6.95 | 16.91 | 100 |
| Emamectin benzoate | Resistant | 202 | 65 | 97 |

These results indicate that selamectin is significantly more potent against sea lice than the commercially available alternative, emamectin benzoate (SLICE®). Sea lice populations, which appear to demonstrate resistance to emamectin benzoate, were highly susceptible to treatment with selamectin. This is a particularly surprising result given the structural and functional similarities between the two macrocyclic lactones.

The invention claimed is:

1. A method for treating a parasitic infection or infestation from sea lice in a fish, the method comprising orally administering to said fish a therapeutically effective amount of about 50-150 µg/kg/day of selamectin with a dietary fish feed admixed with selamectin.

2. The method of claim 1, wherein the sea lice are of the genera Lepeophtheirus and Caligus.

3. The method of claim 2, wherein the sea lice is at least one of Lepeophtheirus salmonis, Caligus celmensi, Caligus curtus, Caligus dussumieri, Caligus elongates, Caligus longicaudatus, Caligus rogercresseyi or Caligus stromii.

4. The method of claim 1 wherein the fish is a farmed fish and is selected from the group consisting of carp, tuna, tilapia, cod, halibut, trout, and salmon.

5. The method of claim 4 wherein the fish feed is further admixed with an oil that is selected from a fish oil or vegetable oil.

* * * * *